United States Patent
Kinuta

(10) Patent No.: US 9,526,882 B2
(45) Date of Patent: Dec. 27, 2016

(54) PERCUTANEOUS ADMINISTRATION DEVICE AND METHOD FOR PRODUCING THE SAME

(75) Inventor: Seichin Kinuta, Tochigi (JP)

(73) Assignee: OPTNICS PRECISION CO., LTD., Ashikaga-shi, Tochigi (JP)

( * ) Notice: Subject to any disclaimer, the term of this patent is extended or adjusted under 35 U.S.C. 154(b) by 183 days.

(21) Appl. No.: 13/695,290

(22) PCT Filed: Apr. 27, 2011

(86) PCT No.: PCT/JP2011/060271
§ 371 (c)(1),
(2), (4) Date: Oct. 30, 2012

(87) PCT Pub. No.: WO2011/138917
PCT Pub. Date: Nov. 10, 2011

(65) Prior Publication Data
US 2013/0046244 A1  Feb. 21, 2013

(30) Foreign Application Priority Data

May 1, 2010  (JP) .................................. 2010-106038

(51) Int. Cl.
*A61M 35/00* (2006.01)
*A61K 8/67* (2006.01)
(Continued)

(52) U.S. Cl.
CPC ............ *A61M 35/003* (2013.01); *A61K 8/676* (2013.01); *A61Q 19/02* (2013.01); *A61K 9/703* (2013.01);
(Continued)

(58) Field of Classification Search
CPC .... A61K 9/703; A61K 9/7084; A61K 9/7092; A61M 2037/0007; A61M 35/00
(Continued)

(56) References Cited

U.S. PATENT DOCUMENTS

2002/0098228 A1* 7/2002 Tarazi .................. A61K 9/7084
424/449
2005/0181029 A1* 8/2005 Mitragotri ............ A61K 9/7092
424/448
(Continued)

FOREIGN PATENT DOCUMENTS

JP  10-137319 A  5/1998
JP  2003-238347 A  8/2003
(Continued)

OTHER PUBLICATIONS

Japanese Office Action dated Dec. 17, 2013 issued for the corresponding Japanese Patent Application No. 2012-513812.
(Continued)

*Primary Examiner* — Tatyana Zalukaeva
*Assistant Examiner* — Andrew J Mensh
(74) *Attorney, Agent, or Firm* — SOLARIS Intellectual Property Group, PLLC

(57) ABSTRACT

A main body (10) of a percutaneous administration device is formed from a resilient biodegradable resin, such as an elastomer resin or a silicone rubber, and includes a substrate (12) and multiple micropiles (14) formed on the substrate. The leading ends of each micropile (14) is shaped with a flat contact face (14A) that stops upon the contact with the skin and does not perforate the skin. Depressed portions (18) are formed in the contact face (14A). The depressed portions hold a functional substance (16) having a whitening effect, such as powdered or liquid vitamin C or provitamin C, or fine ceramic particles impregnated with vitamin C.

8 Claims, 26 Drawing Sheets

(51) Int. Cl.
  *A61Q 19/02* (2006.01)
  *A61K 9/00* (2006.01)
  *A61K 9/24* (2006.01)
  *A61K 9/70* (2006.01)
  *A61M 37/00* (2006.01)

(52) U.S. Cl.
  CPC ............ *A61K 9/7084* (2013.01); *A61K 9/7092* (2013.01); *A61K 2800/87* (2013.01); *A61M 35/00* (2013.01); *A61M 2037/0007* (2013.01)

(58) Field of Classification Search
  USPC .................................. 604/290; 424/400, 473
  See application file for complete search history.

(56) References Cited

U.S. PATENT DOCUMENTS

| | | | |
|---|---|---|---|
| 2007/0031495 A1* | 2/2007 | Eppstein et al. | 424/473 |
| 2008/0131492 A1* | 6/2008 | Nangia et al. | 424/449 |
| 2010/0028388 A1* | 2/2010 | Gibson et al. | 424/400 |

FOREIGN PATENT DOCUMENTS

| | | |
|---|---|---|
| JP | 2004-290574 A | 10/2004 |
| JP | 2005-103113 A | 4/2005 |
| JP | 2007-130417 A | 5/2007 |
| WO | 2008083423 A | 7/2008 |
| WO | 2010022252 A | 2/2010 |

OTHER PUBLICATIONS

Extended European Search Report dated Mar. 21, 2014 from the EPO in an European patent application corresponding to the instant patent application.

\* cited by examiner

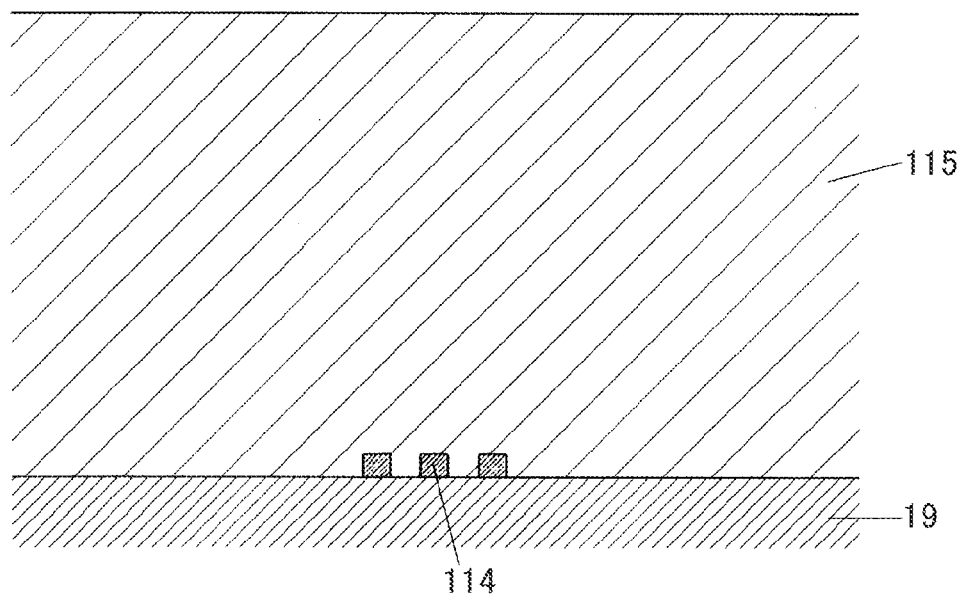
FIG.9F
FIG.9G
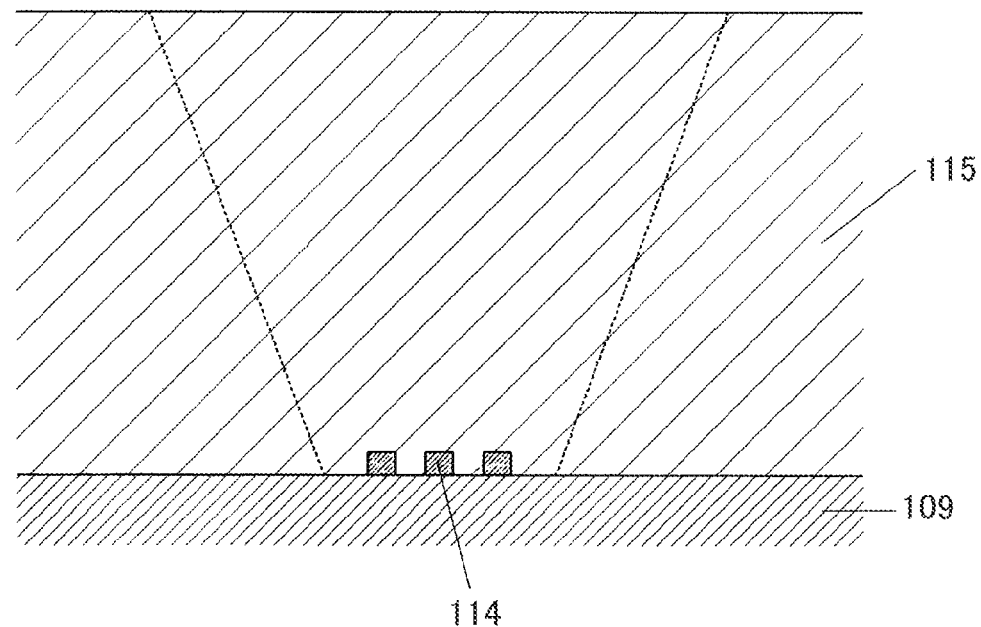

PERCUTANEOUS ADMINISTRATION DEVICE AND METHOD FOR PRODUCING THE SAME

TECHNICAL FIELD

The present invention relates to a percutaneous administration device that imparts decorative and/or functional effects such as whitening, for example to make blemishes occurring on the epidermis of the skin disappear safely or to smooth out wrinkles, and to a manufacturing method for the percutaneous administration device.

BACKGROUND ART

Hitherto, substances in powdered or liquid form have been surface coated in order to impart decorative and/or functional effects such as whitening to the stratum corneum of the epidermis of the skin. Accordingly, external factors such as sweating and meteorological conditions inevitably lead to a marked drop or fluctuation in the function of such substances.

Accordingly, as methods that are not influenced by the external factors above, methods are proposed that employ functional micropiles manufactured using X-ray lithography processes, electrocasting processes, and injection molding processes (see patent documents 1 and 2).

Patent document 1: Japanese Patent Application Laid-Open (JP-A) No. 2003-238347
Patent document 2: JP-A No. 2007-130417

DISCLOSURE OF INVENTION

Technical Problem

The present invention provides a percutaneous administration device having what is referred to as percutaneous ability. Percutaneous ability is the ability to pass through the stratum corneum of the epidermis to reach blemishes at the bottom of the epidermis, enabling a medicinal solution of an emulsifier capable of getting rid of for example blemishes occurring in the epidermis or capable of smoothing wrinkles to exhibit its capabilities by passing through the skin without damaging the skin and without the need to perform disinfection. The present invention also provides a manufacturing method for the percutaneous administration device.

Solution to Problem

A first aspect of the present invention includes a resilient main body with a contact face that stops on contact with skin, and a depressed portion that is formed at the contact face and that retains a functional substance inside the depressed portion.

In the above aspect a leading end of the percutaneous administration device does not pierce the skin since the contact face provided to the resilient main body stops on contact with the skin. There is accordingly no damage to the skin and no need perform disinfection. The functional substance retained in the depressed portion of the contact face is dabbed against the epidermis of the skin and penetrates to the stratum corneum, and an affected site of, for example, a blemish on the epidermis of the skin can be made to disappear and whitened, and/or wrinkles can be smoothed due to the decorative and/or functional effect of the functional substance. Moreover, with methods in which a functional substance in sheet form is dabbed onto the epidermis of the skin by leading ends of micropiles, the functional substance is wasted since the functional substance sheet is used once and then changed. However, in the present invention the functional substance is retained by the depressed portion and so the functional substance can be used effectively and without waste.

A second aspect of the present invention includes a main body retention mechanism that retains the main body in a state in which the contact face is in contact with the skin, and that presses the functional substance inside the depressed portion towards a skin side.

In the above aspect the main body is retained to the skin with the contact face in a state of contact with the skin and the functional substance inside the depressed portion is pushed towards the skin side by the main body retention mechanism. The capability of the functional substance to penetrate to the stratum corneum of the skin can accordingly be enhanced.

A third aspect of the present invention includes a skin pressing portion formed projecting inside the depressed portion with a leading end portion of the skin pressing portion pressing against the skin.

In the above aspect, the capability of the functional substance to penetrate to the stratum corneum of the skin can be enhanced due to the leading end portion of the skin pressing portion formed projecting inside the depressed portion that presses against the skin.

In a fourth aspect of the present invention the main body retention mechanism is an adhesive tape, the adhesive tape including a main body retention portion that retains the main body and a skin adhesion portion that adheres to the skin.

In the above aspect, the main body can be reliably stuck to the skin due to the main body retention mechanism being the adhesive tape including the main body retention portion that retains the main body and the skin adhesion portion that adheres to the skin.

In a fifth aspect of the present invention the main body retention mechanism is a suction adhesion portion that is formed at the main body and adheres to the skin by suction.

In the above aspect, the main body can easily be stuck to the skin without employing for example adhesive tape since the main body retention mechanism is the suction adhesion portion that is formed at the main body and adheres to the skin by suction.

In a sixth aspect of the present invention the skin pressing portion includes an edge shaped at a peripheral edge portion of a location on the skin pressing portion that contacts the skin.

In the above aspect, the stratum corneum of the skin is stimulated by the edge formed at the peripheral edge portion of the location on the skin pressing portion that contacts the skin. The capability of the functional substance to penetrate to the stratum corneum of the skin can accordingly be further enhanced.

A seventh aspect of the present invention includes a protective sheet that covers the contact face and the depressed portion, and that can be peeled off when the main body is being stuck to the skin.

In the above aspect, the contact face and the functional substance inside the depressed portion can be protected by the protective sheet when in a state of storage since the protective sheet that covers the contact face and the depressed portion can be peeled off when the main body is being contacted with the skin.

An eighth aspect of the present invention includes forming a micropile pattern including a depressed portion by exposing a photosensitive resin to light, producing a micropile mold of a reverse shape to the micropile pattern by performing an electrocasting process, and injection molding the percutaneous administration device by employing the micropile mold.

In the above aspect, a low cost method can be employed in which an ultraviolet sensitive resin is exposed to ultraviolet light for forming the micropile pattern, due to forming the micropile pattern including the depressed portion by exposing a photosensitive resin to light, producing the micropile mold of a reverse shape to the micropile pattern by performing the electrocasting process, and injection molding the percutaneous administration device by employing the micropile mold.

Advantageous Effects of Invention

As described above, according to the first aspect of the present invention, the skin is not damaged and there is no need to perform disinfection since the leading end of the percutaneous administration device does not pierce the skin. Moreover, the functional substance can be used without waste due to the functional substance being retained in the depressed portion. Through the simple method of dabbing the leading end of the percutaneous administration device against the epidermis, the excellent advantageous effects can be obtained of smoothing out wrinkles or getting rid of and whitening an affected site of a blemish in the skin surface layer due to the decorative and/or functional effects of the functional substance.

According to the second aspect of the present invention, the capability of the functional substance to penetrate to the stratum corneum of the skin is enhanced.

According to the third aspect of the present invention, the capability of the functional substance to penetrate to the stratum corneum of the skin is enhanced.

According to the fourth aspect of the present invention, reliable adhesion to the skin can be achieved.

According to the fifth aspect of the present invention, adhesion to the skin can be easily accomplished.

According to the sixth aspect of the present invention, the capability of the functional substance to penetrate to the stratum corneum of the skin is further enhanced.

According to the seventh aspect of the present invention, the contact face and the functional substance inside the depressed portion can be protected in a state of storage.

According to the eighth aspect of the present invention, ultraviolet light can be employed to form the micropile pattern. In terms of expenditure invested in manufacturing equipment, an ultraviolet device costs only several million Japanese yen and an ultraviolet mask costs only in the region of 100,000 Japanese yen, this being an incomparably low cost at around one ten-thousandth that of an X-ray device. It is accordingly easier to invest in equipment, as a result of which percutaneous administration devices can be provided at a low price, with the excellent advantageous effects of facilitating consumer purchases of the percutaneous administration device and allowing such percutaneous administration devices to become widespread.

BRIEF DESCRIPTION OF DRAWINGS

FIG. 9F is a drawing illustrating a manufacturing process of a percutaneous administration device of the first exemplary embodiment of the present invention.

FIG. 9G is a drawing illustrating a manufacturing process of a percutaneous administration device of the first exemplary embodiment of the present invention.

BEST MODE FOR CARRYING OUT THE INVENTION

Explanation follows regarding exemplary embodiments of the present invention, however the present invention is not limited by any of the exemplary embodiments below.

First Exemplary Embodiment

Figure 1:
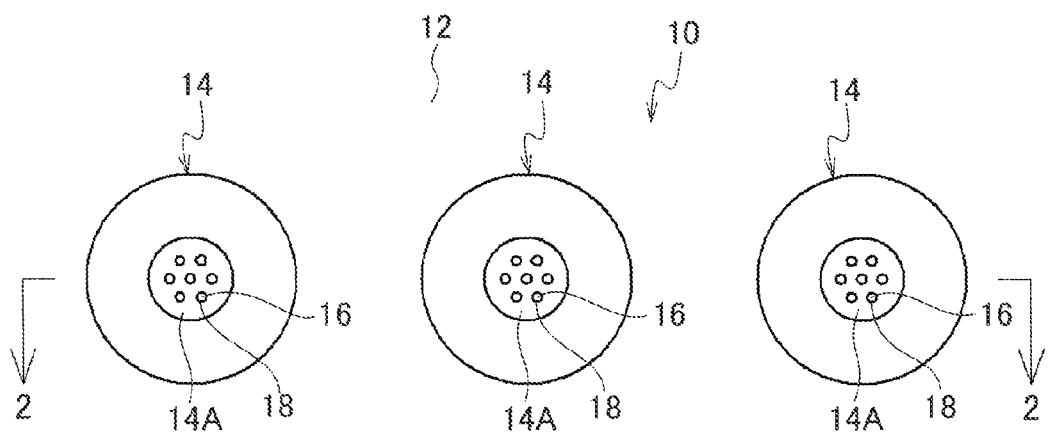
FIG. 1 is a plan view of a percutaneous administration device of a first exemplary embodiment of the present invention.
Figure 2:
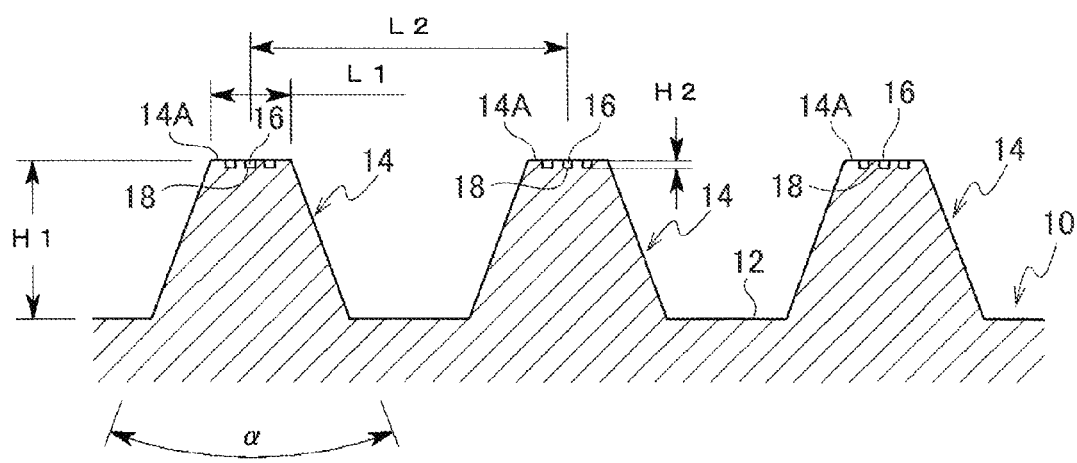
FIG. 2 is a cross-section taken along line 2-2 of FIG. 1.
Figure 3:
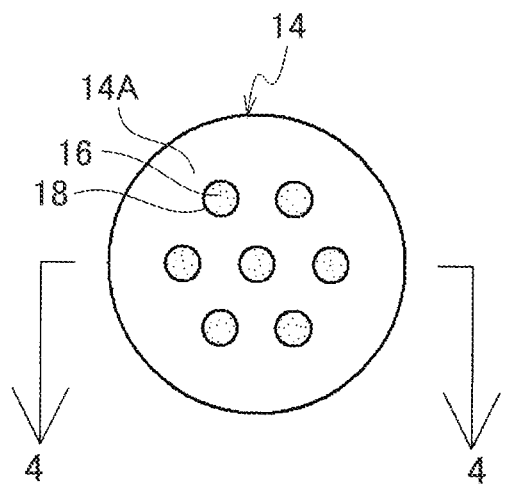
FIG. 3 is an enlarged drawing of relevant portions of FIG. 1.
Figure 4:
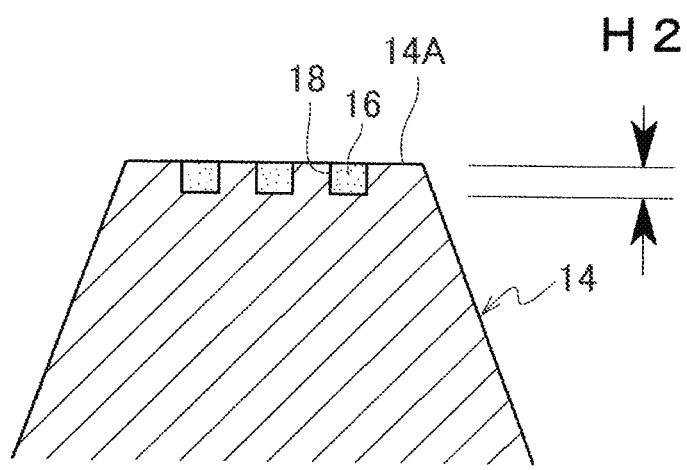
FIG. 4 is a cross-section taken along line 4-4 of FIG. 3.

A main body 10 of a percutaneous administration device illustrated in FIG. 1 and FIG. 2 is resilient. The main body 10 is formed, for example, from a resilient biodegradable resin such as an elastomer resin or a silicone rubber. The main body 10 includes a substrate 12 and plural micropiles 14 provided on the substrate 12. A leading end of each micropile 14 is configured as a flattened contact face 14A that stops on contact with skin without piercing the skin. The contact faces 14A are for example formed with 7 dimple shaped depressed portions 18. As shown in FIG. 3 and FIG. 4, the depressed portions 18 are filled with and retain a functional substance 16. The functional substance 16 has a whitening effect and is a substance such as vitamin C or provitamin C in a powdered or liquid form, or fine ceramic particles impregnated with vitamin C.

Note that a large number of the micropiles 14 of the present exemplary embodiment are provided on the substrate 12 in order to adequately supply the functional substance to the stratum corneum of the epidermis of the skin. For example, 10 000 of the micropiles 14 are provided per 1 $cm^2$ of the substrate 12.

By way of an example, the depressed portions 18 are formed by providing circular holes to the contact face 14A as shown in FIG. 3. As shown in FIG. 2 and FIG. 4, a length (height) H1 of the micropiles 14 is between 50 μm and 600 μm, a depth H2 of the depressed portions 18 is between 10 μm and 200 μm, an angle α of the micropiles 14 is 40°, a diameter L1 of each contact face 14A is 0.1 mm, and a separation L2 between micropiles 14 is 0.4 mm.

Second Exemplary Embodiment

Figure 5:
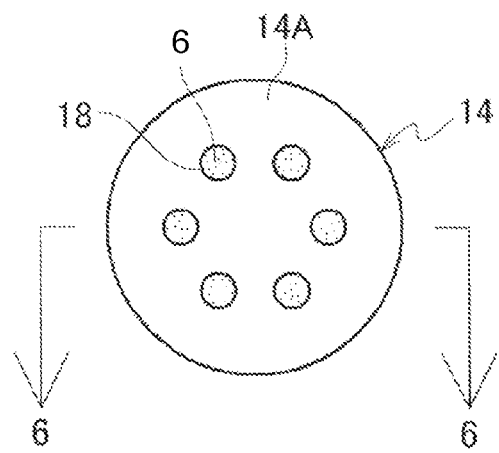
FIG. 5 is a plan view corresponding to FIG. 3, illustrating a percutaneous administration device of a second exemplary embodiment of the present invention.
Figure 6:
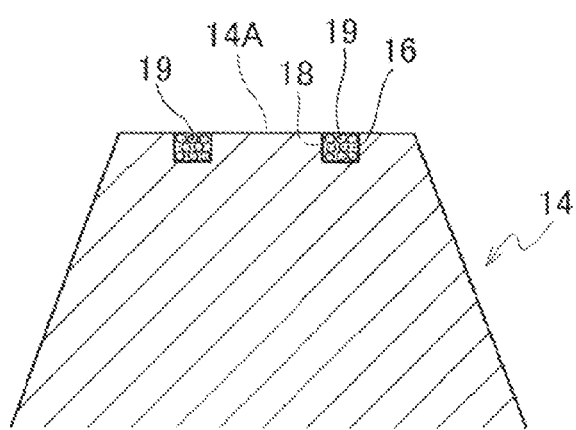
FIG. 6 is a cross-section taken along line 6-6 of FIG. 5.

As shown in FIG. 5 and FIG. 6, in a second exemplary embodiment the number of circular holes of depressed portions 18 may be a number other than 7, for example 6.

Also, as shown in FIG. 6, the insides of the depressed portions 18 may be filled with silica gel 19, and the silica gel 19 impregnated with a functional substance 16 in order to enhance the retainability of the functional substance 16.

Third Exemplary Embodiment

Figure 7:
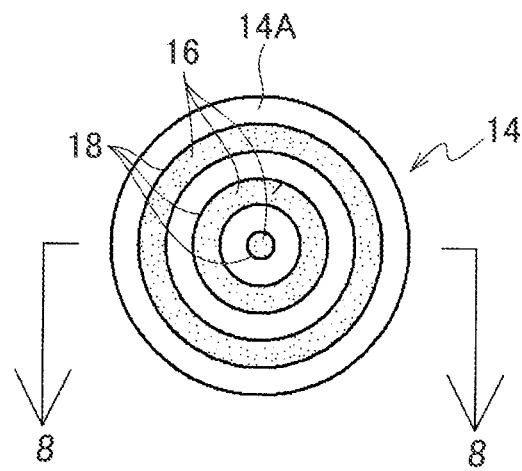
FIG. 7 is a plan view corresponding to FIG. 3, illustrating a percutaneous administration device of a third exemplary embodiment of the present invention.
Figure 8:
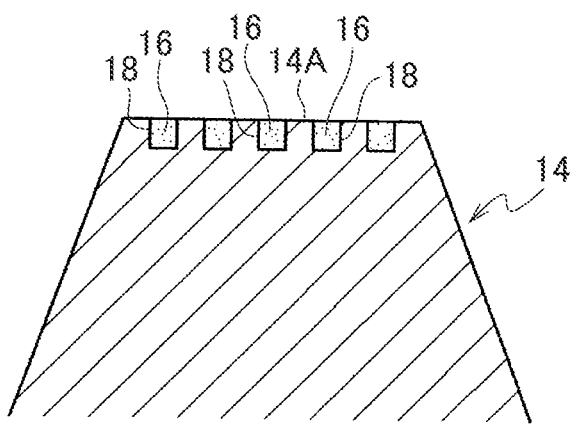
FIG. 8 is a cross-section taken along line 8-8 of FIG. 7.

As shown in FIG. 7 and FIG. 8, in a third exemplary embodiment depressed portions 18 may be formed by a circular hole and plural ring shaped grooves centered around the circular hole.

(Manufacturing Method)

FIG. 9A to FIG. 9M illustrate an example of a manufacturing process for the percutaneous administration device of the first exemplary embodiment. The manufacturing process includes forming a micropile pattern including depressed portions by exposing a photosensitive resin to light, producing a micropile mold of a reverse shape to the micropile pattern by performing an electrocasting process, and injection molding the percutaneous administration device by employing the micropile mold.

Figure 9A:
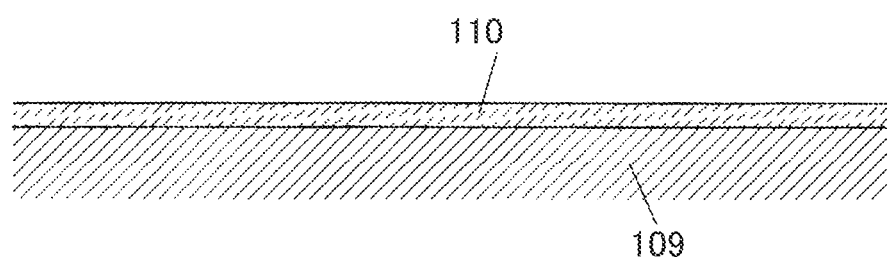
FIG. 9A is a drawing illustrating a manufacturing process of a percutaneous administration device of the first exemplary embodiment of the present invention.
Figure 9B:
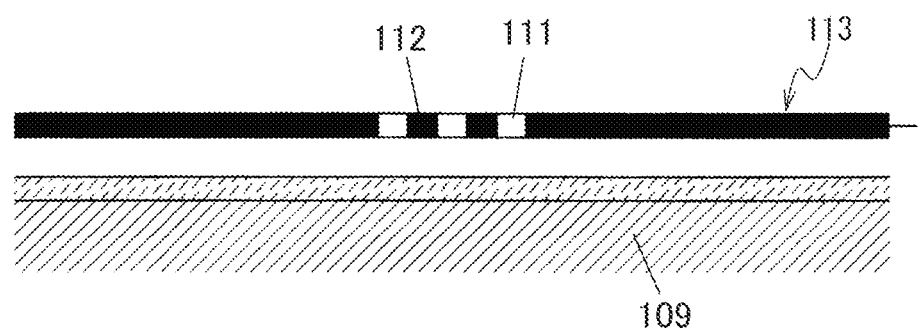
FIG. 9B is a drawing illustrating a manufacturing process of a percutaneous administration device of the first exemplary embodiment of the present invention.
Figure 9C:
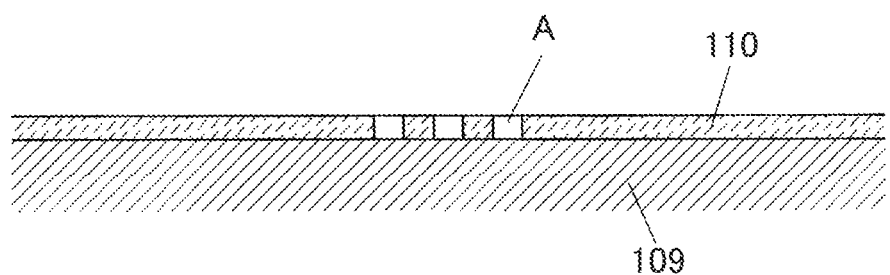
FIG. 9C is a drawing illustrating a manufacturing process of a percutaneous administration device of the first exemplary embodiment of the present invention.
Figure 9D:
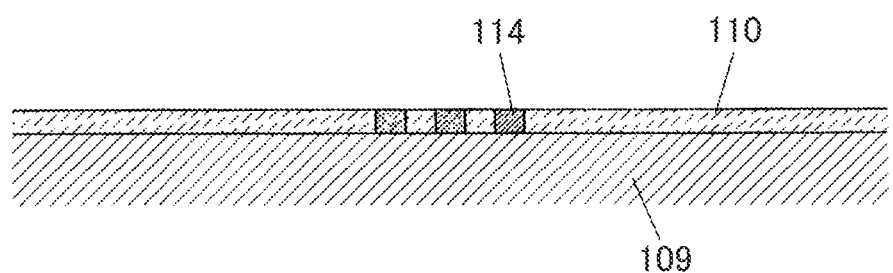
FIG. 9D is a drawing illustrating a manufacturing process of a percutaneous administration device of the first exemplary embodiment of the present invention.
Figure 9E:
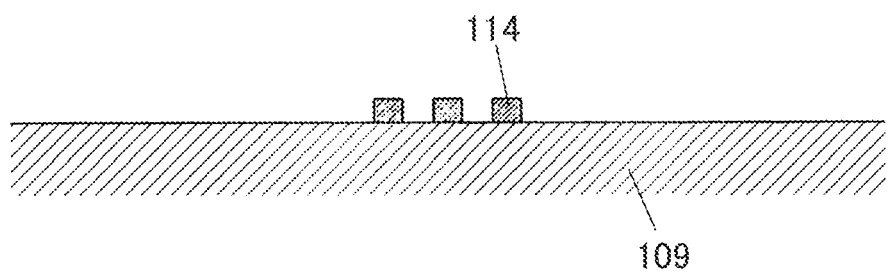
FIG. 9E is a drawing illustrating a manufacturing process of a percutaneous administration device of the first exemplary embodiment of the present invention.

More precisely, in FIG. 9A a resist (an ultraviolet-light-sensitive resin) 110 is coated on a stainless steel base 109. In FIG. 9B, ultraviolet light is illuminated from above through a lithography mask 113 that has white portions 111 and black portions 112, dissolving A portions as shown in FIG. 9C by exposure to ultraviolet light passing through the white portions 111. Next, in FIG. 9D, copper 114 is electrocoated inside the A portions by electrocasting, after which the resist 100 is dissolved by a solvent in FIG. 9E. Then, in FIG. 9F, a negative working resist 115 is coated.

Figure 9H:
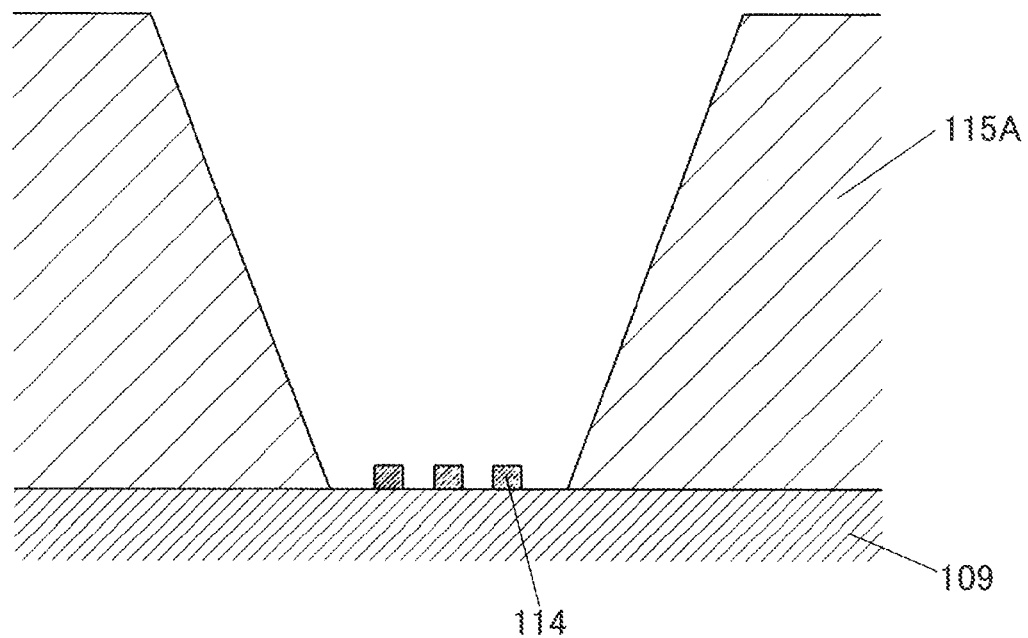
FIG. 9H is a drawing illustrating a manufacturing process of a percutaneous administration device of the first exemplary embodiment of the present invention.
Figure 9I:
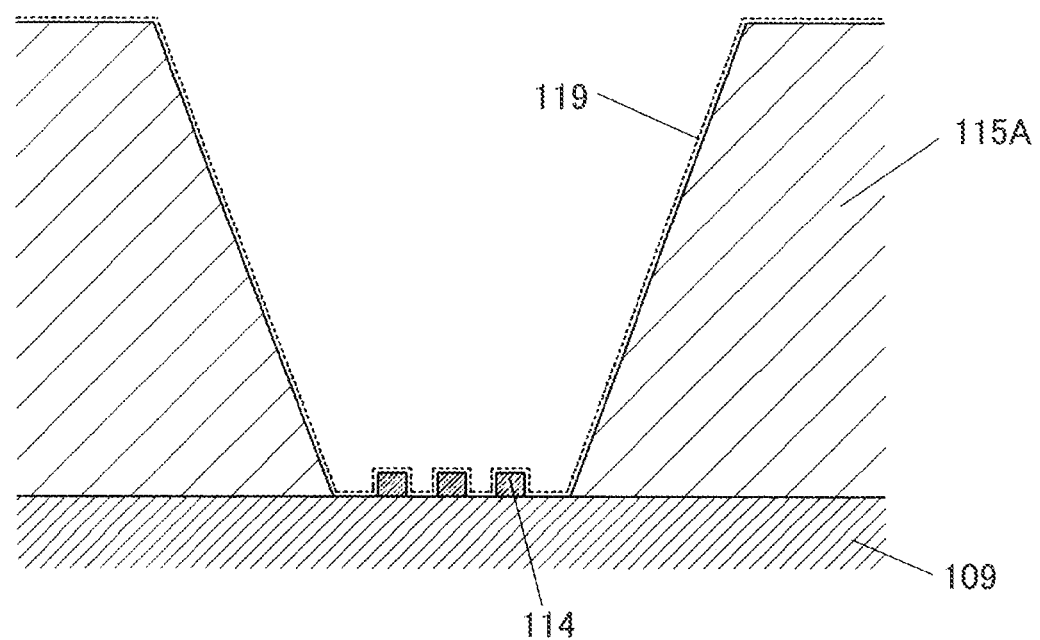
FIG. 9I is a drawing illustrating a manufacturing process of a percutaneous administration device of the first exemplary embodiment of the present invention.
Figure 9J:
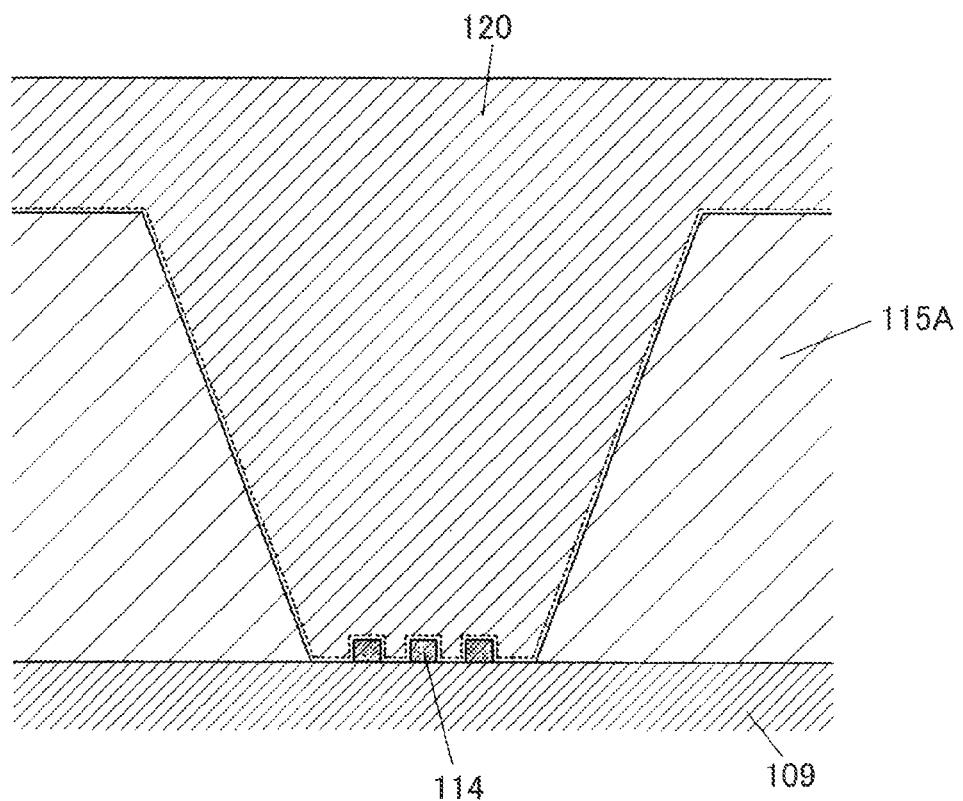
FIG. 9J is a drawing illustrating a manufacturing process of a percutaneous administration device of the first exemplary embodiment of the present invention.

Next, in FIG. 9G, a lithography mask 118 that has white portions 116 and black portions 117 is employed for rotation exposure whilst being tilted in the directions indicated by the arrows, forming an inclined negative working resist 115A as shown in FIG. 9H. Then, in FIG. 9I, the entire face is then coated with copper 119 by vapor deposition to provide conductivity, and then nickel 120 is electrocoated by electrocasting in FIG. 9J.

Figure 9K:
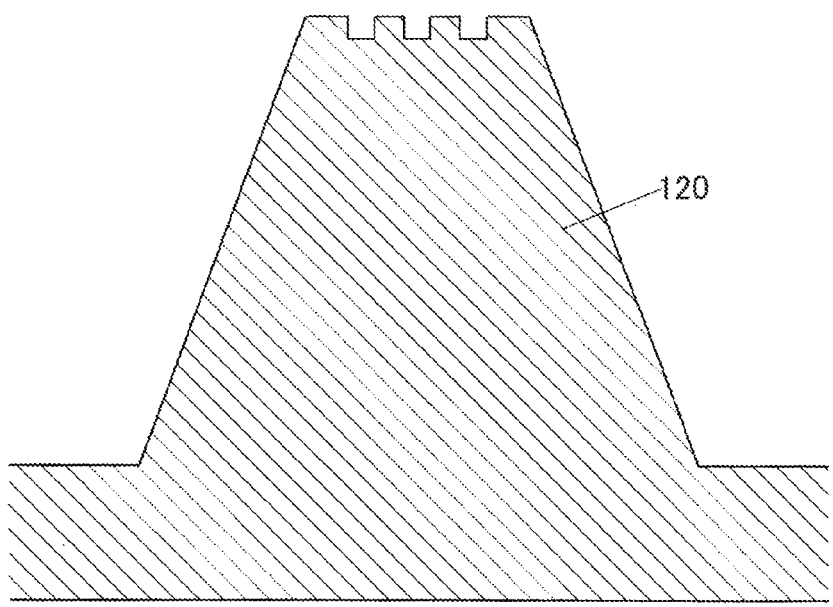
FIG. 9K is a drawing illustrating a manufacturing process of a percutaneous administration device of the first exemplary embodiment of the present invention.
Figure 9L:
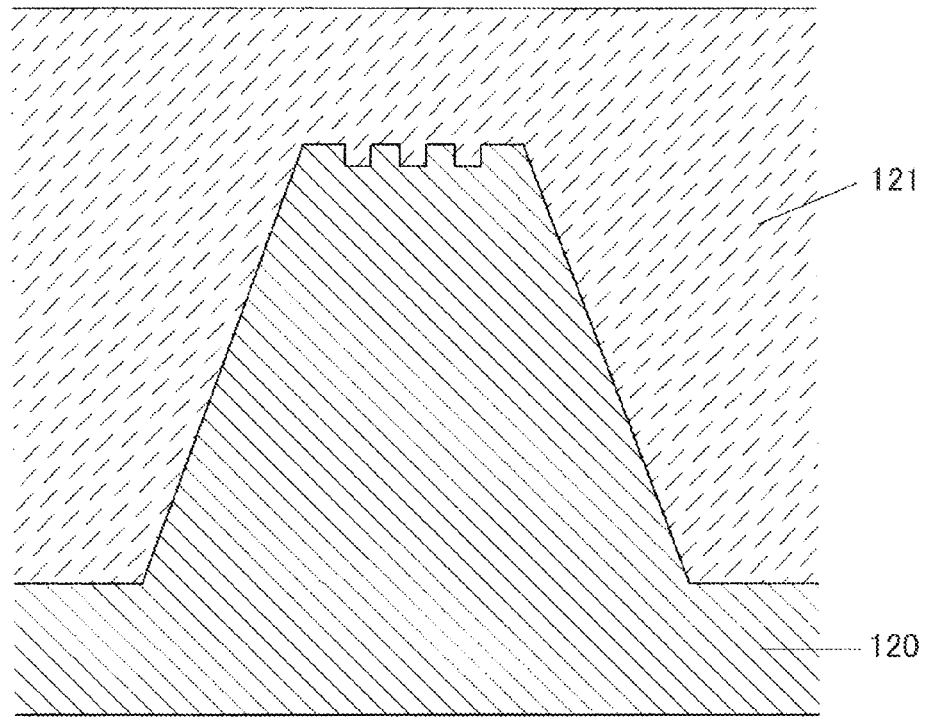
FIG. 9L is a drawing illustrating a manufacturing process of a percutaneous administration device of the first exemplary embodiment of the present invention.
Figure 9M:
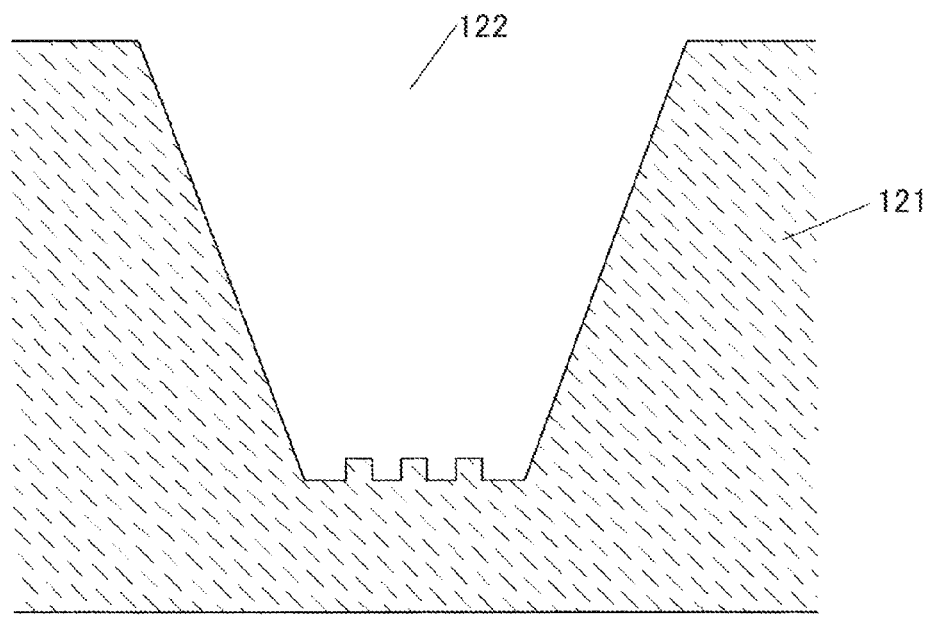
FIG. 9M is a drawing illustrating a manufacturing process of a percutaneous administration device of the first exemplary embodiment of the present invention.

Next, the negative resist 115 is dissolved by a solvent, the copper 114 is removed by etching, and a nickel mold 120 as shown in FIG. 9K is achieved by flipping vertically. In FIG. 9L, nickel 121 is then electrocoated by electrocasting, and in FIG. 9M, the nickel mold 120 is removed and the micropile mold 121 is completed by flipping vertically. The percutaneous administration device with depressed portions is injection molded by filling a recess 122 of the micropile mold 121 with a resilient biodegradable resin, such as an elastomer resin or a silicone rubber.

(Operation)

Explanation follows regarding operation of the present exemplary embodiment configured as described above. As shown in FIG. 4, the functional substance 16 that is a whitener in powdered or liquid form is filled into and retained by the depressed portions 18 formed in the contact faces 14A of the micropiles 14 on the main body 10 of the percutaneous administration device. Next, the substrate 12 of the main body 10 of the percutaneous administration device is held in the hand and the contact faces 14A of the micropiles 14 are dabbed against blemishes occurring on the skin of, for example the face or arm of a subject. After lightly tapping several times, the main body 10 of the percutaneous administration device is removed from the skin, ending whitening treatment. Wrinkle smoothing treatment can also be performed if a wrinkle smoothing substance is employed as the functional substance 16 and dabbed against wrinkles, similarly to as described above.

In the present exemplary embodiment, during treatment the leading ends of the micropiles 14 stop when simply dabbed against the skin of the subject, and do not pierce the skin. Treatment is accordingly painless with no need to perform disinfection after treatment since there are no puncture wounds.

As a result of this treatment, the functional substance 16, which is a similar color to the skin of the subject and has been filled into and retained by the depressed portions 18 of the micropiles 14, penetrates to the stratum corneum of the epidermis of an affected site of the subject. Then, after a specific time period has elapsed, the modifying and/or functional effects due to the functional substance are exhibited and the disappearance of blemishes is confirmed.

Fourth Exemplary Embodiment

Figure 10:
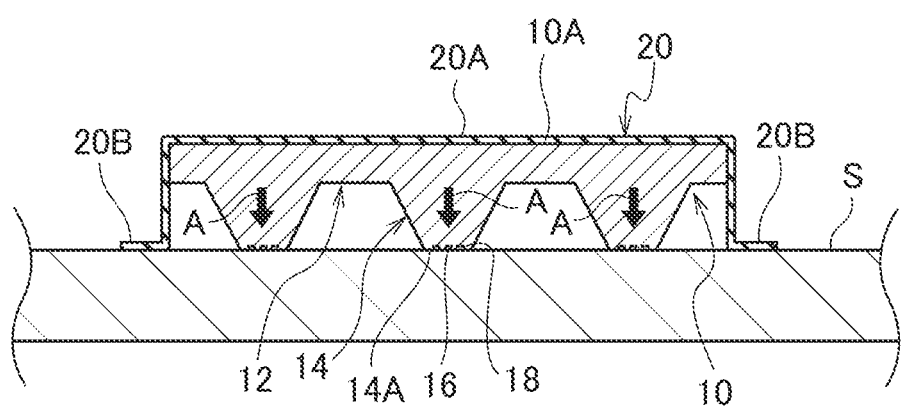
FIG. 10 is a cross-section illustrating a usage state of a percutaneous administration device of a fourth exemplary embodiment of the present invention.

Explanation follows regarding a fourth exemplary embodiment, illustrated in FIG. 10. Note that features similar to the first exemplary embodiment are appended with the same reference numerals and explanation thereof is omitted. As shown in FIG. 10, in the present exemplary embodiment, an adhesive tape 20 is attached to a main body 10 of the percutaneous administration device as an example of a main body retention mechanism. The adhesive tape 20 includes a main body retention portion 20A that retains the main body 10 provided to a central portion of the adhesive tape 20, and a skin adhesion portion 20B provided at peripheral edge portions of the adhesive tape 20 for adhering to skin S. The main body retention portion 20A is adhered to a rear face 10A of the main body 10. Contact faces 14A of micropiles 14 accordingly stop in contact with the skin S due to the skin adhesion portion 20B of the adhesive tape 20 adhering to the skin S. The main body 10 can accordingly be retained in a state stuck to the skin S, and the functional substance 16 inside the depressed portions 18 can be pressed towards the skin S side (the arrow A direction in FIG. 10).

The ability of the functional substance 16 to penetrate to the stratum corneum of the epidermis can accordingly be enhanced in the present exemplary embodiment due to the adhesive tape 20 retaining the contact faces of the micropiles 14 in a state of contact with the skin S and due to the functional substance 16 inside the depressed portions 18 being pressed towards the skin S side.

Fifth Exemplary Embodiment

Figure 11:
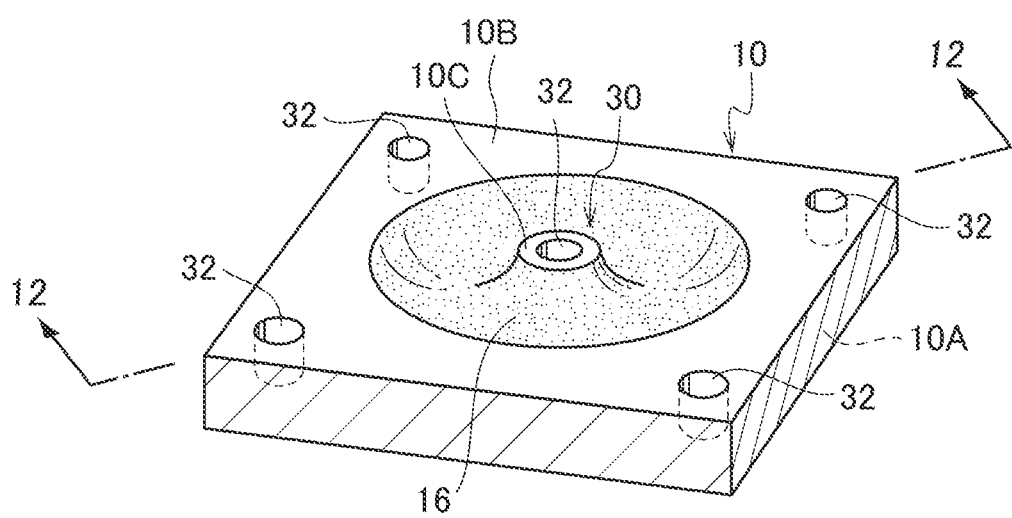
FIG. 11 is a perspective view illustrating a percutaneous administration device of a fifth exemplary embodiment of the present invention.
Figure 12:
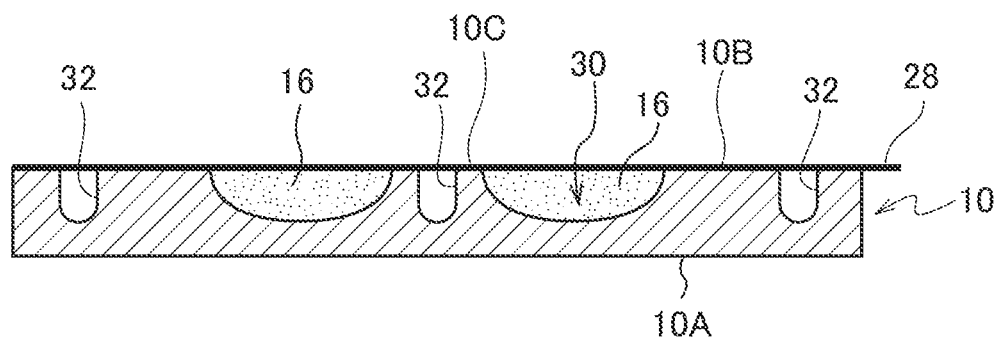
FIG. 12 is a cross-section taken along line 12-12 of FIG. 11, with a protective sheet added.
Figure 13:
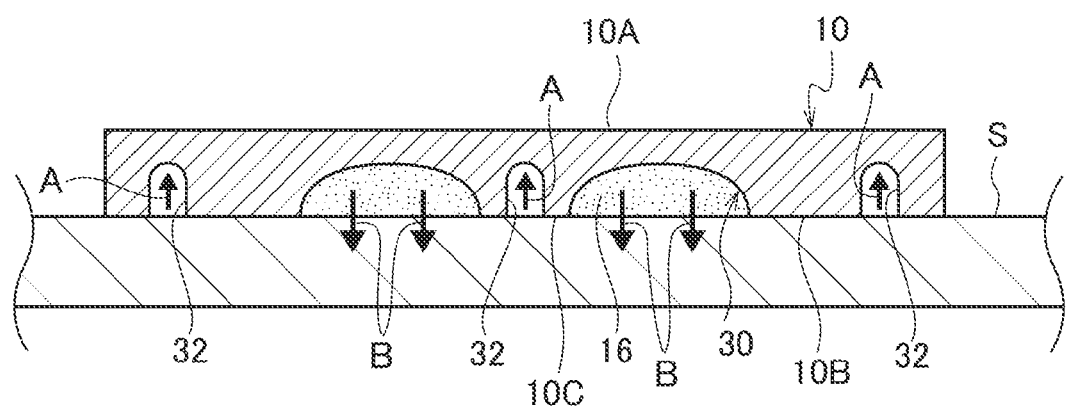
FIG. 13 is a cross-section illustrating a usage state of a percutaneous administration device of the fifth exemplary embodiment of the present invention.

Explanation follows regarding a fifth exemplary embodiment, illustrated in FIG. 11 to FIG. 13. Note that features similar to the first exemplary embodiment are appended with the same reference numerals and explanation thereof is omitted.

As shown in FIG. 11, in the present exemplary embodiment depressed portions 30 are formed at a contact face 10B, that stops on contact with skin without piercing the skin, of a main body 10 of a percutaneous administration device. Note that although not shown in the drawing, plural of the depressed portions 30 are formed at the contact face 10B. As shown in FIG. 11, the depressed portions 30 are configured in a ring shape in plan view, and as shown in FIG. 12, the depressed portions 30 are configured with a hemispherical shape as viewed in cross-section. The functional substance 16 is retained inside the respective depressed portions 30. Central portions of the depressed portions 30 are configured with a circular contact face 10C that stops on contact with skin and does not pierce the skin.

Suction adhesion portions 32 are formed as an example of a main body retention mechanism at an outer peripheral portion of each of the depressed portions 30 on the contact face 10B at specific separations around the peripheral direction, for example at separations of 90°. A suction adhesion portion 32 is also formed at a central portion of the contact face 10C.

As shown in FIG. 12, the suction adhesion portions 32 are formed by providing circular holes in the thickness direction of the main body 10 of the percutaneous administration device. As shown by the arrows A in FIG. 13, the suction adhesion portions 32 adhere the main body 10 of the percutaneous administration device to the skin S by suction due to resilient deformation.

The main body 10 of the percutaneous administration device is further provided with a protective sheet 28 covering the contact faces 10B, 10C and the depressed portions 30. The protective sheet 28 is configured such when sticking the main body 10 of the percutaneous administration device to the skin S, the protective sheet 28 can be peeled off and the main body 10 of the percutaneous administration device then stuck to the skin S after the protective sheet 28 has been peeled off.

Accordingly in the present exemplary embodiment, the main body 10 of the percutaneous administration device can be retained due to the suction adhesion portions 32, in a state stuck to the skin S with the contact faces 10B, 10C in a state of contact with the skin S, and with the functional substance 16 inside the depressed portions 30 being pressed towards the skin S side as shown by the arrows B in FIG. 13. The ability of the functional substance 16 to penetrate to the stratum corneum of the epidermis can accordingly be enhanced.

Since in the present exemplary embodiment the main body retention mechanism is configured by the suction adhesion portions 32 that are formed at the main body 10 of the percutaneous administration device and that adhere to the skin S by suction, the main body 10 of the percutaneous administration device can easily be stuck to the skin S without the use of for example adhesive tape.

In the present exemplary embodiment, the contact faces 10B, 10C of the main body 10 of the percutaneous administration device and the functional substance 16 inside the depressed portions 30 can be protected by the protective sheet 28 during a state of storage.

Sixth Exemplary Embodiment

Figure 14:
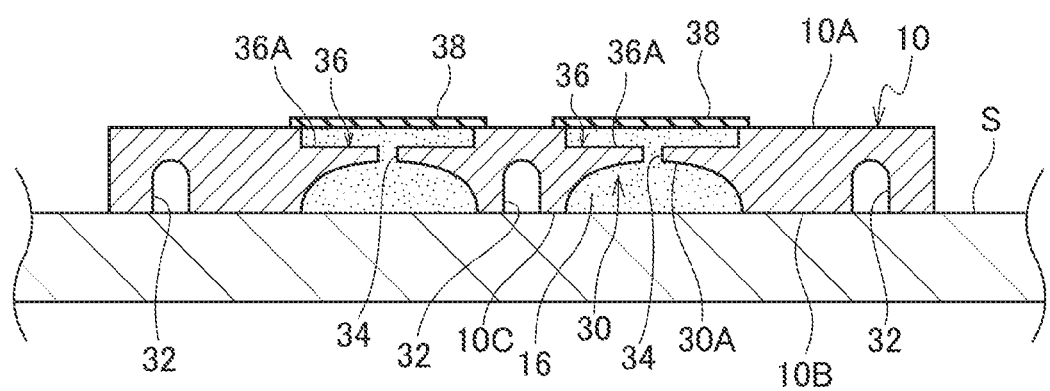
FIG. 14 is a cross-section illustrating a usage state of a percutaneous administration device of a sixth exemplary embodiment of the present invention.

Explanation follows regarding a sixth exemplary embodiment, illustrated in FIG. 14. Note that features similar to the fifth exemplary embodiment are appended with the same reference numerals and explanation thereof is omitted.

As shown in FIG. 14, in the present exemplary embodiment plural through holes 34 are formed at bottom portions 30A of depressed portions 30 at specific separations around the circumferential direction. As an example of a functional substance retention portion, shallow grooves 36 are also formed at a rear face 10A of a main body 10 at locations on the opposite side to the depressed portions 30. The through holes 34 are in communication with bottom portions 36A of the grooves 36. The grooves 36 are closed off by lids 38, and a functional substance 16 is filled into and retained inside the grooves 36, similarly to inside the depressed portions 30.

The lids 38 are formed from a resilient resin such as an elastomer resin or a silicone rubber, similarly to a main body 10. Note that the material for the lids 38 is not limited to being the same material as that of the main body 10, and a different material may be employed.

In the present exemplary embodiment, the functional substance 16 can accordingly also be retained in the grooves 36 as well as in the depressed portions 30, thereby enabling the amount of the functional substance 16 penetrating to the stratum corneum of the epidermis to be increased. Note that by pressing the lid 38 with a fingertip, functional substance 16 inside the grooves 36 can also be made to move to inside the depressed portions 30 through the through holes 34.

Seventh Exemplary Embodiment

Figure 15:
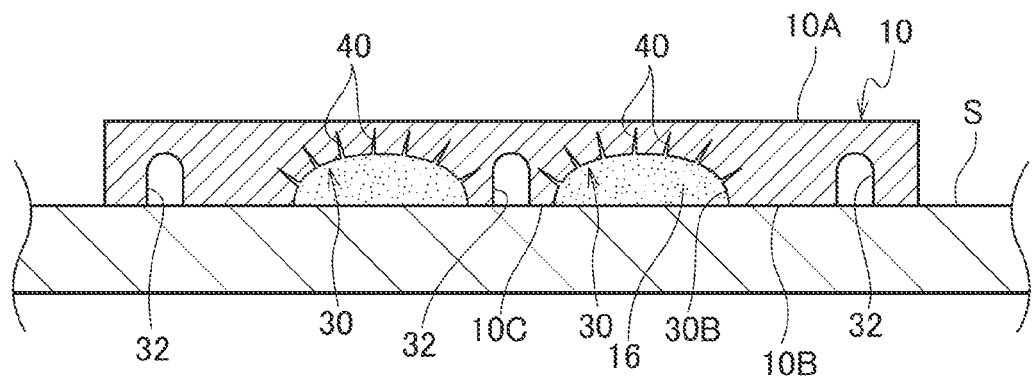
FIG. 15 is a cross-section illustrating a usage state of a percutaneous administration device of a seventh exemplary embodiment of the present invention.

Explanation follows regarding a seventh exemplary embodiment, illustrated in FIG. 15. Note that features similar to the fifth exemplary embodiment are appended with the same reference numerals and explanation thereof is omitted.

As shown in FIG. 15, in the present exemplary embodiment plural fine cracks 40 are formed at inner peripheral portions 30B of depressed portions 30, heading in an outward direction from the depressed portions 30, as an example of functional substance retention portions. The cracks 40 each extend in a straight line from an opening side towards a leading end side, with an opening width that narrows on progression from the opening side towards the leading end side.

Note that the shape of the cracks 40 is not limited to a shape extending in a straight line from the opening side towards the leading end side, and configuration may be made with shapes that extend from the opening side towards the leading end side whilst bending or curving.

In the present exemplary embodiment, a functional substance 16 can accordingly retained in the cracks 40 as well as in the depressed portions 30, thereby enabling the amount of the functional substance 16 penetrating to the stratum corneum of the epidermis to be increased. Due to the cracks 40 being fine, a functional effect of encouraging the functional substance 16 to be delivered slowly and evenly can be promoted.

Eighth Exemplary Embodiment

Figure 16:
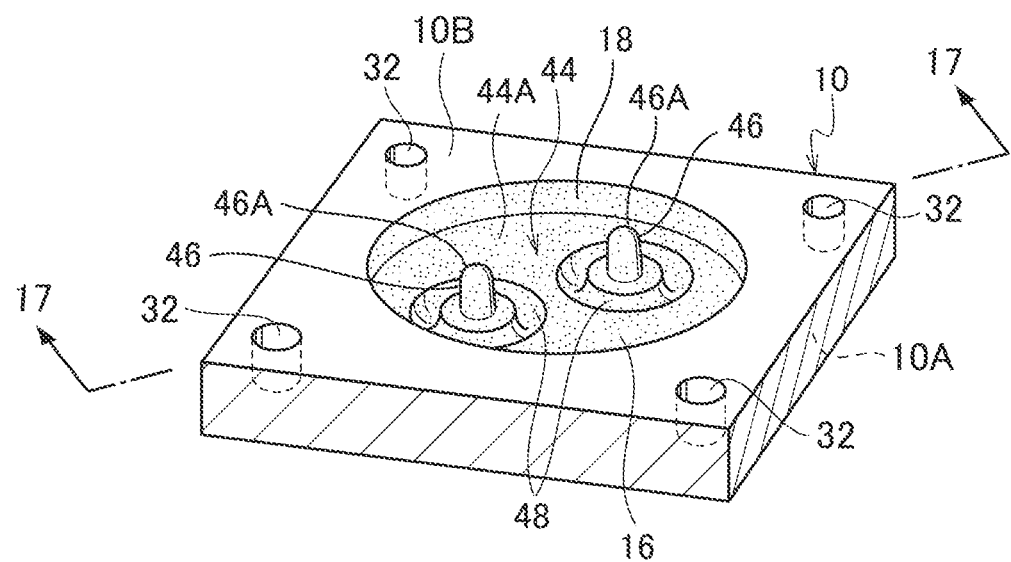
FIG. 16 is a perspective view illustrating a percutaneous administration device of an eighth exemplary embodiment of the present invention.
Figure 17:
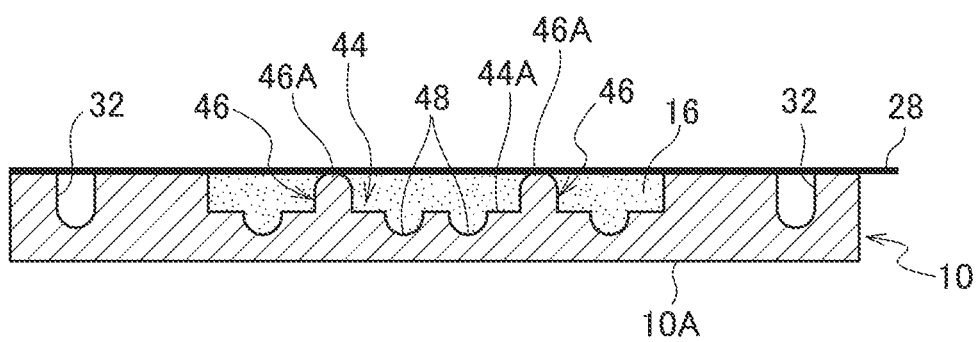
FIG. 17 is a cross-section taken along line 17-17 of FIG. 16, with a protective sheet added.
Figure 18:
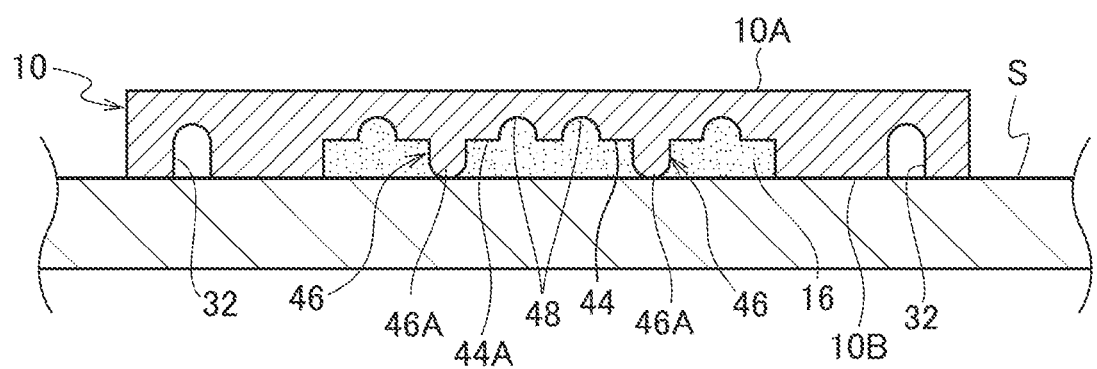
FIG. 18 is a cross-section illustrating a usage state of a percutaneous administration device of the eighth exemplary embodiment of the present invention.

Explanation follows regarding an eighth exemplary embodiment, illustrated in FIG. 16 to FIG. 18. Note that features similar to the fifth exemplary embodiment are appended with the same reference numerals and explanation thereof is omitted.

As shown in FIG. 16 and FIG. 17, in the present exemplary embodiment depressed portions 44 are formed at a contact face 10B, that stops on contact with the skin without piercing the skin, of a main body 10 of a percutaneous administration device. Note that although not shown in the drawings, plural of the depressed portions 44 are formed at the contact face 10B. As shown in FIG. 16, the depressed portions 44 are formed in a circular column shape. A functional substance 18 is retained inside respective depressed portions 44. Skin pressing portions 46 are formed projecting from a bottom portion 44A inside each of the depressed portions 44. A leading end portion 46A of each of the skin pressing portions 46 has a rounded face, and is configured to press against the skin. Note that in the present exemplary embodiment illustrated in FIG. 16, 2 of the skin pressing portions 46 are formed, however the skin pressing portions 46 may number 1 or 3 or more.

Ring shaped grooves 48 are formed in the bottom portions 44A of the depressed portions 44 at an outside peripheral portion of the respective skin pressing portions 46. The functional substance 16 is filled inside the grooves 48, similarly to inside the depressed portions 44.

In the present exemplary embodiment, the ability of the functional substance 16 retained inside the depressed portions 44 and the grooves 48 to penetrate to the stratum corneum of the epidermis is accordingly enhanced since the leading end portions 46A of the skin pressing portions 46 press against the skin.

Note that configuration may be made without forming the grooves 48 in the bottom portions 44A of the depressed portions 44 at outer peripheral portions of the skin pressing portions 46.

Ninth Exemplary Embodiment

Figure 19:
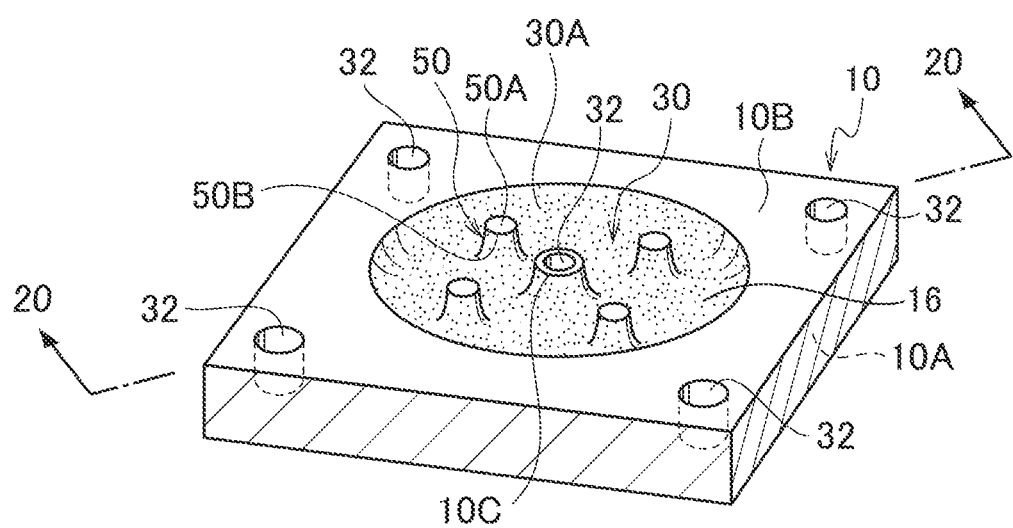
FIG. 19 is a perspective view illustrating a percutaneous administration device of a ninth exemplary embodiment of the present invention.
Figure 20:
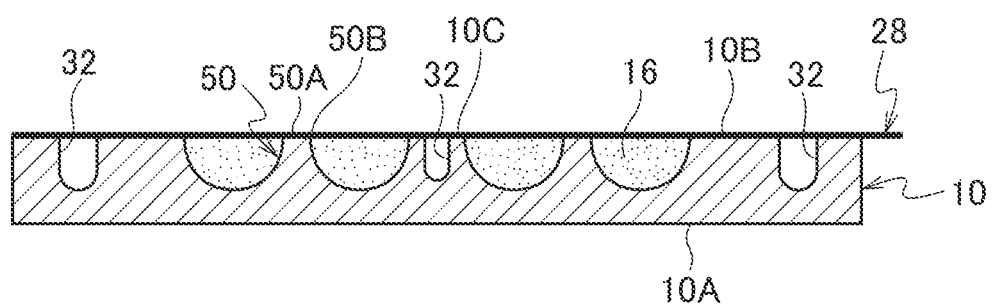
FIG. 20 is a cross-section taken along line 20-20 of FIG. 19, with a protective sheet added.
Figure 21:
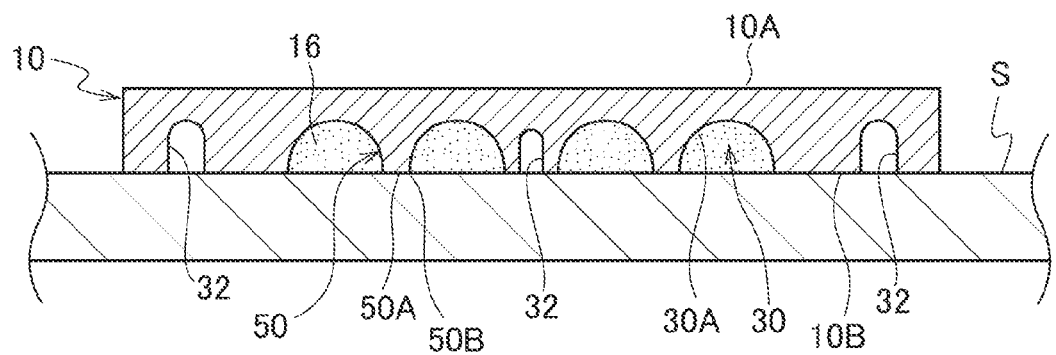
FIG. 21 is a cross-section illustrating a usage state of a percutaneous administration device of the ninth exemplary embodiment of the present invention.

Explanation follows regarding a ninth exemplary embodiment, illustrated in FIG. 19 to FIG. 21. Note that features similar to the fifth exemplary embodiment are appended with the same reference numerals and explanation thereof is omitted.

As shown in FIG. 19 and FIG. 20, in the present exemplary embodiment skin pressing portions 50 are formed projecting from bottom portions 30A of depressed portions 30 in a main body 10 of a percutaneous administration device. Leading ends 50A of the skin pressing portions 50 are configured with circular flat faces, by forming edges (corners) at peripheral edge portions 50B of the leading ends 50A (not formed with rounded shapes), the skin is stimulated such that a functional substance can penetrate readily. Note that 4 of the skin pressing portions 50 are shown in FIG. 19, however the number of skin pressing portions 50 is not limited to 4. The shapes of the leading ends 50A of the skin pressing portions 50 are also not limited to circular shapes, and may be rectangular, for example square shaped.

As shown in FIG. 21, in the present exemplary embodiment edges of the peripheral edge portions 50B of the leading ends 50A of the skin pressing portions 50 stimulate the stratum corneum of the skin. As a result, the ability of a functional substance 16 to penetrate to the stratum corneum is enhanced.

Tenth Exemplary Embodiment

Figure 22:
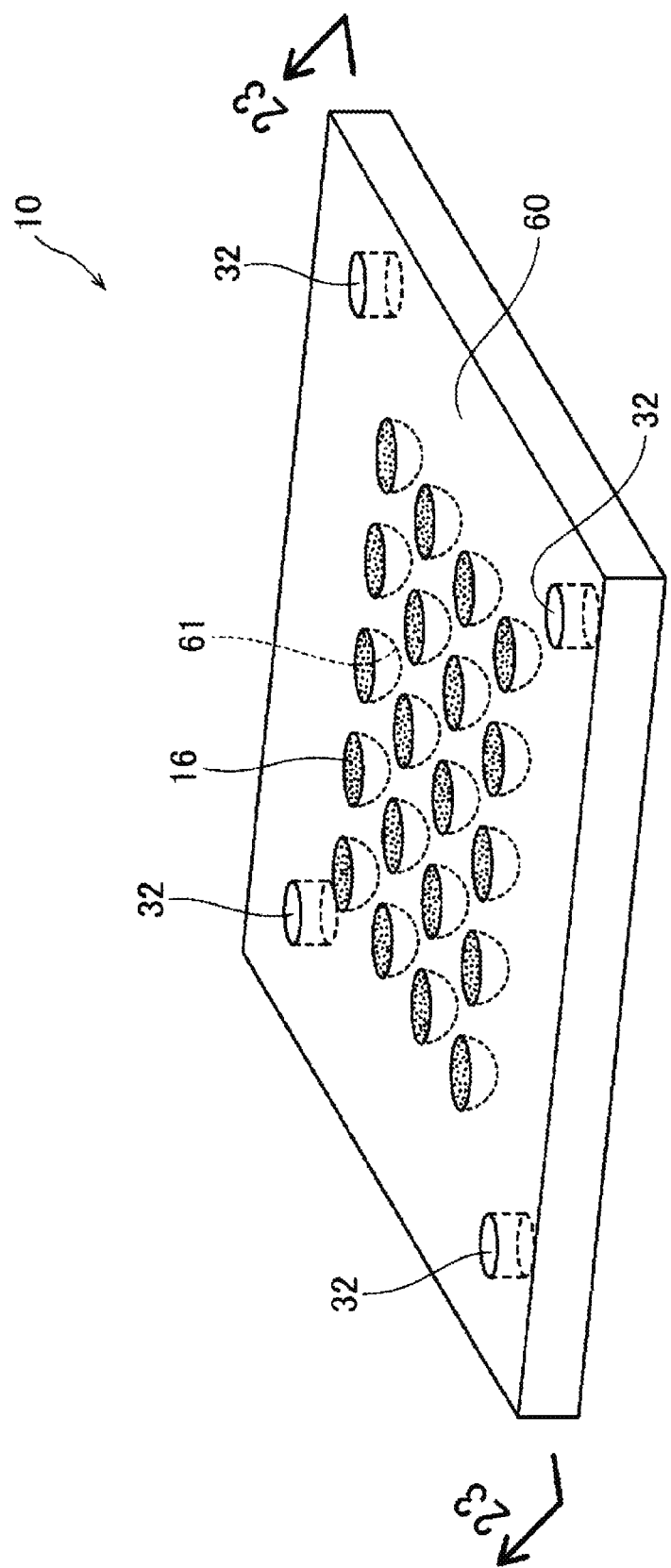
FIG. 22 is a perspective view illustrating a percutaneous administration device of a tenth exemplary embodiment of the present invention.
Figure 23:
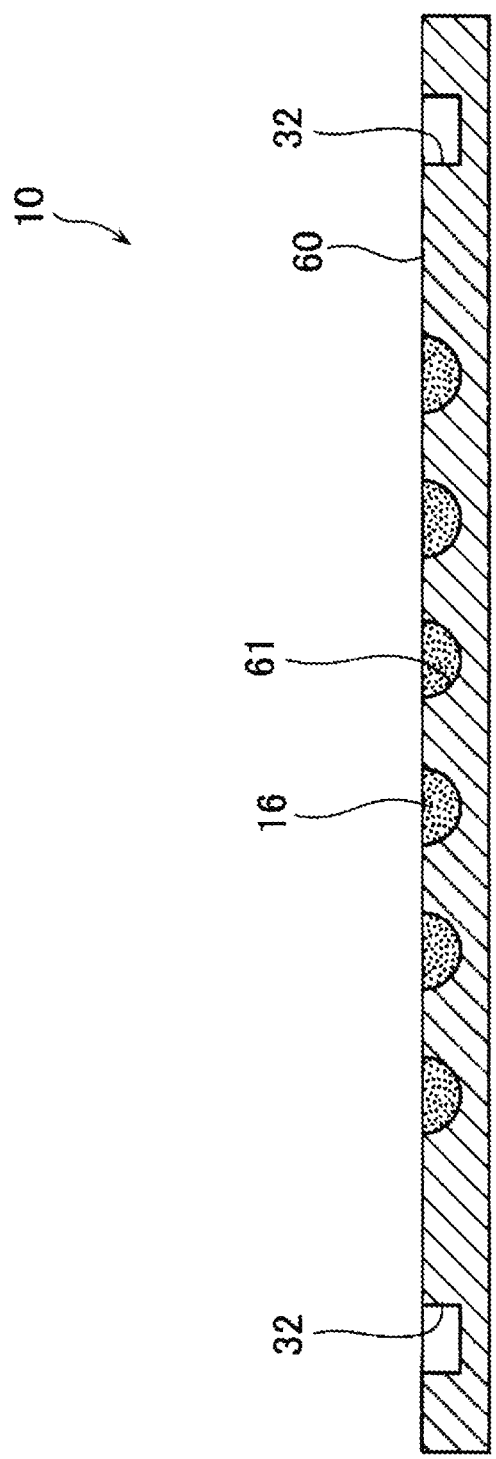
FIG. 23 is a cross-section taken along line 23-23 of FIG. 22.

Explanation follows regarding a tenth exemplary embodiment, illustrated in FIG. 22 and FIG. 23. Note that features similar to the fifth exemplary embodiment are appended with the same reference numerals and explanation thereof is omitted.

In the present exemplary embodiment, suction adhesion portions 32 and several dimple shaped depressed portions 61 are formed at a contact face 60 of a main body 10 of a percutaneous administration device. A functional substance 16 is filled into the several depressed portions 61. The functional substance 16 retained in the depressed portions 61 penetrates to the stratum corneum of the epidermis when the main body 10 is adhered to the skin by suction by the suction adhesion portions 32.

Eleventh Exemplary Embodiment

Figure 24:
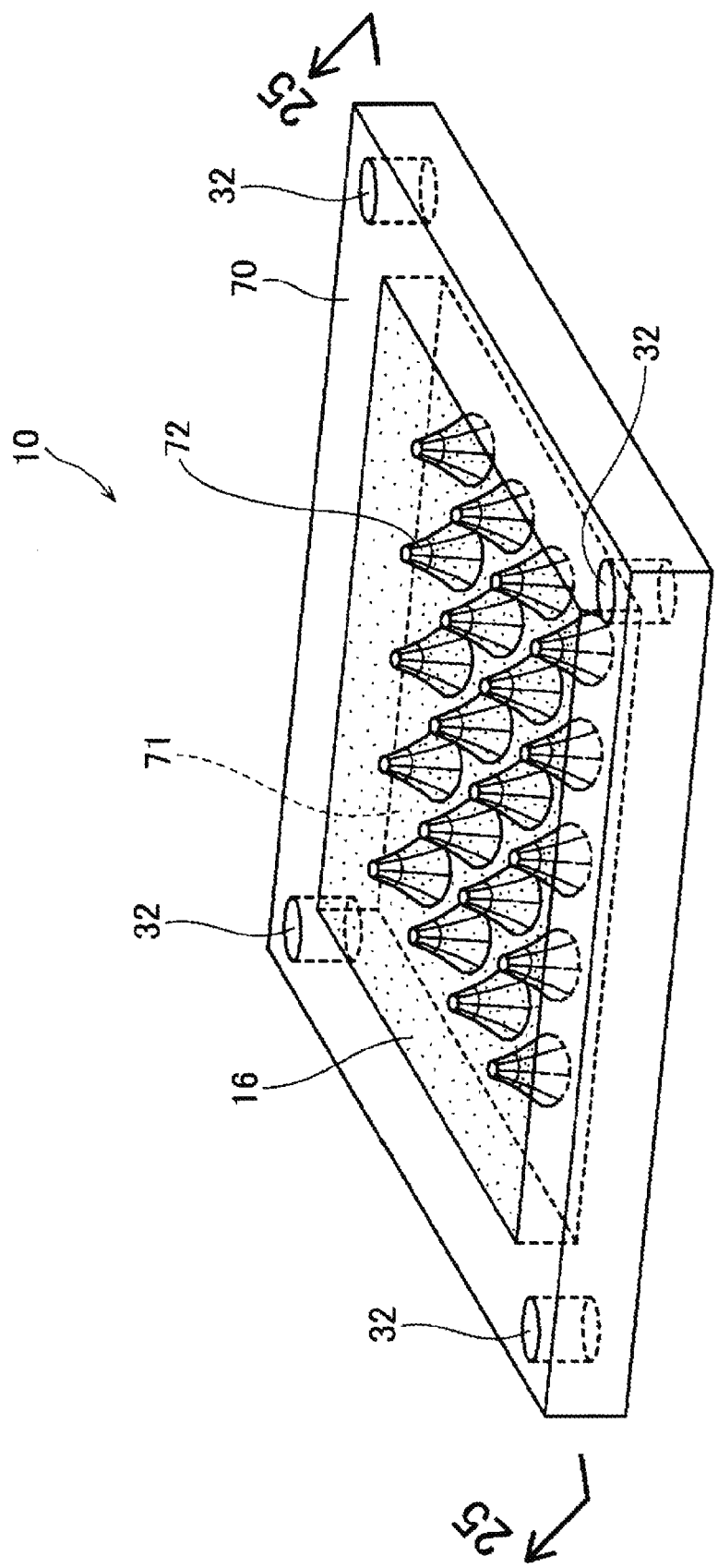
FIG. 24 is a perspective view illustrating a percutaneous administration device of an eleventh exemplary embodiment of the present invention.
Figure 25:
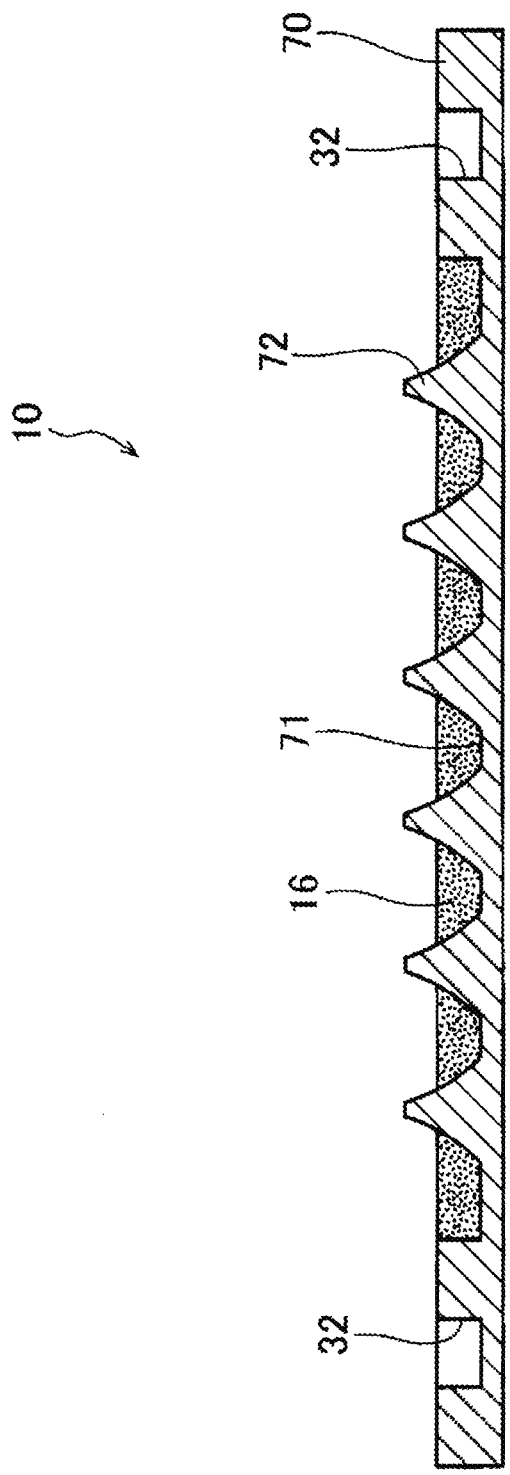
FIG. 25 is a cross-section taken along line 25-25 of FIG. 24.

Explanation follows regarding an eleventh exemplary embodiment, illustrated in FIG. 24 and FIG. 25. Note that features similar to the fifth exemplary embodiment are appended with the same reference numerals and explanation thereof is omitted.

In the present exemplary embodiment, similarly to in the first exemplary embodiment a main body 10 of a percutaneous administration device is formed from a resilient resin such as an elastomer resin or a silicone rubber. A ceramic is contained inside the resin. A peripheral edge portion 70 configuring a contact face is formed with suction adhesion portions 32. Several micropiles 72 serving as skin pressing portions and having a height slightly higher than the peripheral edge portion 70 are formed at a bottom portion of a rectangular box shaped depressed portion 71 formed at the inside of the peripheral edge portion 70. Note that leading ends of the micropiles 72 are configured with flattened contact faces that stop on contact with the skin without piercing the skin. By including a ceramic inside the resin, the micropiles 72 is provided with micropores of the ceramic itself and a functional substance 16 penetrates through the micropores.

The functional substance 16 is accordingly filled into and retained by the depressed portion 71, and when the main body 10 is adhered to the skin under suction of the suction adhesion portions 32, the leading ends of the micropiles 72 of a height higher than the peripheral edge portion 70 press against the skin, and the functional substance 16 that has penetrated from the depressed portion 71 through to the leading ends of the micropiles 72 penetrates through from the stratum corneum of the epidermis.

By forming edges (corners) (not forming rounded shapes) to the peripheral edge portions of the leading ends of the micropiles 72, the skin is stimulated to facilitate penetration of the functional substance 16.

Other Exemplary Embodiments

Detailed explanation has been given above of particular exemplary embodiments of the present invention, however appropriate combinations may be made of any of the above exemplary embodiments. The present invention is also not limited by any of the above exemplary embodiments, and it would be obvious to a practitioner skilled in the art that various other exemplary embodiments are possible within the scope of the present invention.

The invention claimed is:

1. A percutaneous administration device comprising: a resilient main body comprising:
    a contact face, at a periphery of the main body, that stops on contact with skin;
    a depressed portion that retains a functional substance, the functional substance delivered from the depressed portion after the contact face contacts the skin; and
    a skin pressing portion that is located inside the periphery of the main body, that is surrounded by the depressed portion and that projects from an area inside of the depressed portion, a leading end portion of the skin pressing portion stopping on contact with and pressing against the skin and the skin pressing portion forming a suction adhesion portion that is suctioned to the skin, at a skin-contacting surface of the leading end portion.

2. The percutaneous administration device of claim 1, further comprising a main body retention mechanism that retains the main body in a state in which the contact face is in contact with the skin, and that presses the functional substance inside the depressed portion towards a skin side.

3. The percutaneous administration device of claim 2, wherein the main body retention mechanism is an adhesive tape, the adhesive tape comprising a main body retention portion that retains the main body, and a skin adhesion portion that adheres to the skin.

4. The percutaneous administration device of claim 2, wherein the main body retention mechanism is another suction adhesion portion that is formed at the main body and adheres to the skin by suction.

5. The percutaneous administration device of claim 1, wherein the skin pressing portion includes an edge formed at a peripheral edge portion of a location on the skin pressing portion that contacts the skin.

6. The percutaneous administration device of claim 1, further comprising a protective sheet that covers the contact face and the depressed portion, and that can be peeled off when the main body is retained in a state in which the contact face is in contact with the skin.

7. The percutaneous administration device of claim 1, wherein a ring shaped groove is formed in a bottom portion of the depressed portion at an outside peripheral portion of the skin pressing portion.

8. The percutaneous administration device of claim 1, wherein the leading end portion of the skin pressing portion is formed so as to be the same height as the contact face of the main body.

* * * * *